United States Patent [19]
Ohki et al.

[11] Patent Number: 5,921,236
[45] Date of Patent: Jul. 13, 1999

[54] MEDICINE ADMINISTERING DEVICE FOR NASAL CAVITIES

[75] Inventors: Hisatomo Ohki; Shigemi Nakamura, both of Isesaki; Kazunori Ishizeki, Fujimi; Akira Yanagawa, Yokohama, all of Japan

[73] Assignees: Unisia Jecs Corporation, Atsugi; Dott Limited Company, Yokohama, both of Japan

[21] Appl. No.: 08/727,633

[22] PCT Filed: Mar. 11, 1996

[86] PCT No.: PCT/JP96/00596

§ 371 Date: Nov. 1, 1996

§ 102(e) Date: Nov. 1, 1996

[87] PCT Pub. No.: WO96/29109

PCT Pub. Date: Sep. 26, 1996

[30] Foreign Application Priority Data

Mar. 10, 1995 [JP] Japan ..................................... 7-079595

[51] Int. Cl.⁶ .................................................. A61M 15/00
[52] U.S. Cl. .............................. 128/203.15; 128/203.21; 128/203.25; 128/203.12
[58] Field of Search ........................ 128/203.21, 203.15, 128/203.25, 203.12, 203.23, 203.24

[56] References Cited

U.S. PATENT DOCUMENTS

| | | | |
|---|---|---|---|
| 3,906,950 | 9/1975 | Cocozza | 128/203.15 |
| 3,921,637 | 11/1975 | Bennie et al. | 128/203.15 |
| 3,949,751 | 4/1976 | Birch et al. | 128/203.15 |
| 5,619,985 | 4/1997 | Ohki et al. | 128/203.15 |
| 5,634,900 | 6/1997 | Makino et al. | 128/203.15 |
| 5,647,349 | 7/1997 | Ohki et al. | 128/203.15 |
| 5,715,811 | 2/1998 | Ohki et al. | 128/203.21 |

FOREIGN PATENT DOCUMENTS 59-34267  2/1984  Japan .

*Primary Examiner*—John G. Weiss
*Assistant Examiner*—William J. Deane, Jr.
*Attorney, Agent, or Firm*—Foley & Lardner

[57] ABSTRACT

A capsule holder 2 of a medicine administering device 1 for nasal cavities comprises a movable member 8 which is axially movable, and a fixed member 3, in which the movable member 8 is formed at its outer periphery with an external thread 8D which is to be threadedly engaged with an internal thread 19C of a medicine spraying section 19. An air inflow hole H is formed by a perforating end 27A of a pin 27 when a capsule K is thrust into a one-side capsule hole 11, while the movable member 8 is raised so that the perforating end 27A is extracted from the air inflow hole H1 when the capsule holder 2 and the medicine spraying section 19 are incorporated with each other. An air outflow hole H2 is formed by a pin 28. A perforating tool is housed in the medicine administering device 1, in which a hole formation action for the air inflow hole H1 is also made during installation of the capsule K. The whole body can be made compact since the longitudinal dimension of the pin 27, 28 is decreased while the outer peripheral surface of the capsule holder 2 is covered with a pump section 15.

12 Claims, 7 Drawing Sheets

MEDICINE ADMINISTERING DEVICE FOR NASAL CAVITIES

FIELD OF THE INVENTION

The present invention relates to a medicine administering device suitable for administering powder-state medicine, for example, into the nasal cavities of a patient.

BACKGROUND OF THE INVENTION

In general, a method of curing by administering powder-state medicine through nasal cavities can be employed for a patient with nasal allergy, asthma and the like. In this curing method, the powder-state medicine filled in a capsule is administered into the nasal cavities by using an exclusive medicine administering device for nasal cavities.

A conventional medicine administering device to be used for this curing method is shown in Japanese Patent Provisional Publication No. 59-34267.

In this conventional medicine administering device for nasal cavities, a cylindrical member is provided at its air inflow-side with a pump section and is formed at its air outflow-side with a concave-shaped section into which a capsule is to be inserted. A tip end section is fitted to the concave-shaped section, thereby forming a capsule accommodating section which is formed with an air introduction passage through which air is supplied to the capsule accommodating section from the pump section. Further, a cap for fitting around the above-mentioned cylindrical member and the tip end section is provided. The cap has, at its inside, an axially extending pin so that a hole is formed through the capsule when the cap is fit onto the concave-shaped section of the above-mentioned cylindrical member and the tip end section.

In this conventional medicine administering device for nasal cavities, in order to form a hole through the capsule for the purpose of preparation of medicine administration, first the capsule filled with powder-state medicine is inserted in the concave-shaped section of the cylindrical member. Thereafter, the tip end section is fitted in position, thereby locating the capsule in the capsule accommodating section. Then, the cap is installed in such a manner that the pin is inserted into the opening section of the tip end section, thereby forming holes at the axially opposite sides of the capsule under the action of the pin disposed inside the cap.

Next, in order to administer the medicine, the tip end section is inserted into one of the nasal cavities of the patient upon detaching the cap from the cylindrical member. Then, the pump section is pressed so that air from the pump section flows through the air introduction passage into the capsule. Accordingly, medicine in the capsule is conveyed through the opening section into the nasal cavity of the patient. Insertion of the tip end section into the nasal cavity is repeated alternately to both nasal cavities, thereby administering medicine to the patient.

Additionally, in the conventional technique, a clearance is formed between the capsule accommodating section and the capsule so that medicine administration to nasal cavities is made alternately to the left and right nasal cavities so as to prevent all of the medicine in the capsule from being administered under only one pressing action of the pump section. Medicine within the capsule generally is administered after about four pressing actions for one of the nasal cavities.

Now, in the conventional medicine administering device for nasal cavities, medicine is administered to each nasal cavity, and therefore the pressing action of the pump section and insertion of the cylindrical member into each nasal cavity must be repeated many times, making medicine administration laborious.

Furthermore, the hole formation is performed in the capsule in order to prepare for medicine administration, the tip end section is detached from the cylindrical member, and then the capsule is accommodated. The tip end section is reattached, and the cap is fitted around the cylindrical member and the tip end section, thereby accomplishing the hole formation. During medicine administration, after the cap is again detached, the pump section is operated to spray medicine into the nasal cavities. Accordingly, it is required to install and detach the cap, which is somewhat cumbersome.

Moreover, the conventional administering device for nasal cavities includes the cylindrical member, the tip end section, the cap provided axially with the pin for hole formation, and the pump section. This provides problems in that there are a large number of parts and the cap may be lost.

DISCLOSURE OF THE INVENTION

The present invention has been made in view of a variety of problems encountered with conventional techniques and is intended to simplify medicine administration and to provide a compact medicine administering device.

A medicine administering device for nasal cavities, according to the present invention comprises capsule holding means including a movable member which is axially movable relative to a fixed member, in a state to hold a capsule whose inside is filled with powder-like medicine; pump means disposed to the fixed member of the capsule holding means to supply air toward the capsule holding means; medicine spraying means disposed to the movable member of the capsule holding means and having a medicine passage whose tip end serves as a spraying hole so as to spray the medicine within the capsule into a nasal cavity of a patient under the influence of air supplied from the pump means; first perforating means disposed to the capsule holding means so as to form an air inflow hole in the capsule; and second perforating means disposed to the medicine spraying means to be axially movable so as to form an air outflow hole in the capsule.

Accordingly, in the perforating action for the capsule, first the air inflow hole of the capsule is formed under the action of the first perforating means by thrusting the capsule to cause the capsule to be held in the movable member, and then the air outflow hole of the capsule can be formed under the action of the second perforating means by axially moving the second perforating means after the medicine spraying means is incorporated with the movable member. Consequently, the capsule holes can be easily formed under the simple operations.

Additionally, in the medicine administration action, air is supplied from the pump means to the capsule holding means, in which this air flows through the air inflow hole, the inside of the capsule and the air outflow hole, and the medicine within the capsule is transferred together with the air into the nasal cavity of the patient through the medicine passage and the spraying hole of the medicine spraying means. By this, the medicine can be simultaneously administered into the left and right nasal cavities of the patient, thereby largely reducing the preparation actions and the medicine administration actions of the patient.

Additionally, by bifurcating the medicine passage of the medicine spraying means to two portions whose tip ends serve respectively as separate spraying holes, in the medicine administration actions, air from the pump means flows through the air inflow hole, the inside of the capsule and the air outflow hole. The medicine within the capsule is supplied together with this air to the left and right nasal cavities of the patient through the respective medicine passages and the spraying holes of the medicine spraying means, thereby making it possible to simultaneously administer the medicine into the left and right nasal cavities of the patient and facilitating medicine administration actions.

Further, the movable member is arranged to be located to the side of the pump means before incorporation while located to the side of the medicine spraying means after incorporation. Accordingly, the air inflow hole is formed in the capsule under the action of the first perforating means in a state where the movable member is moved to the side of the pump means. Thereafter, the movable member is moved to the side of the medicine spraying means so that the first perforating means inserted in the air inflow hole of the capsule is extracted from the air inflow hole, by incorporating the medicine spraying means and the capsule holding means. The air inflow hole of the capsule is simultaneously formed under the action of installing the capsule to the movable member, thus omitting preparation operations thereby lightening load applied to the patient in medicine administration operations.

Further, the pump means is disposed to cover the capsule holding means, and therefore the axial dimension of the medicine administering device for nasal cavities can be decreased, thereby forming the medicine administering device compact.

Furthermore, since the medicine trapping section is formed in the capsule holding means, the medicine to drop into the pump means during perforation is trapped by the medicine trapping section, in which this trapped medicine can be transferred together with the medicine within the capsule through the capsule holding means and the medicine spraying section into the left and right nasal cavities of the patient under the influence of air from the pump section during medicine administration action, thereby reducing the amount of the medicine to be left in the medicine administering device for nasal cavities, thus making it possible to administer a predetermined amount of the medicine within the capsule.

BEST MODE FOR CARRYING OUT THE INVENTION

An embodiment of the present invention will be discussed hereinafter with reference to FIGS. 1 to 7.

Figure 1:
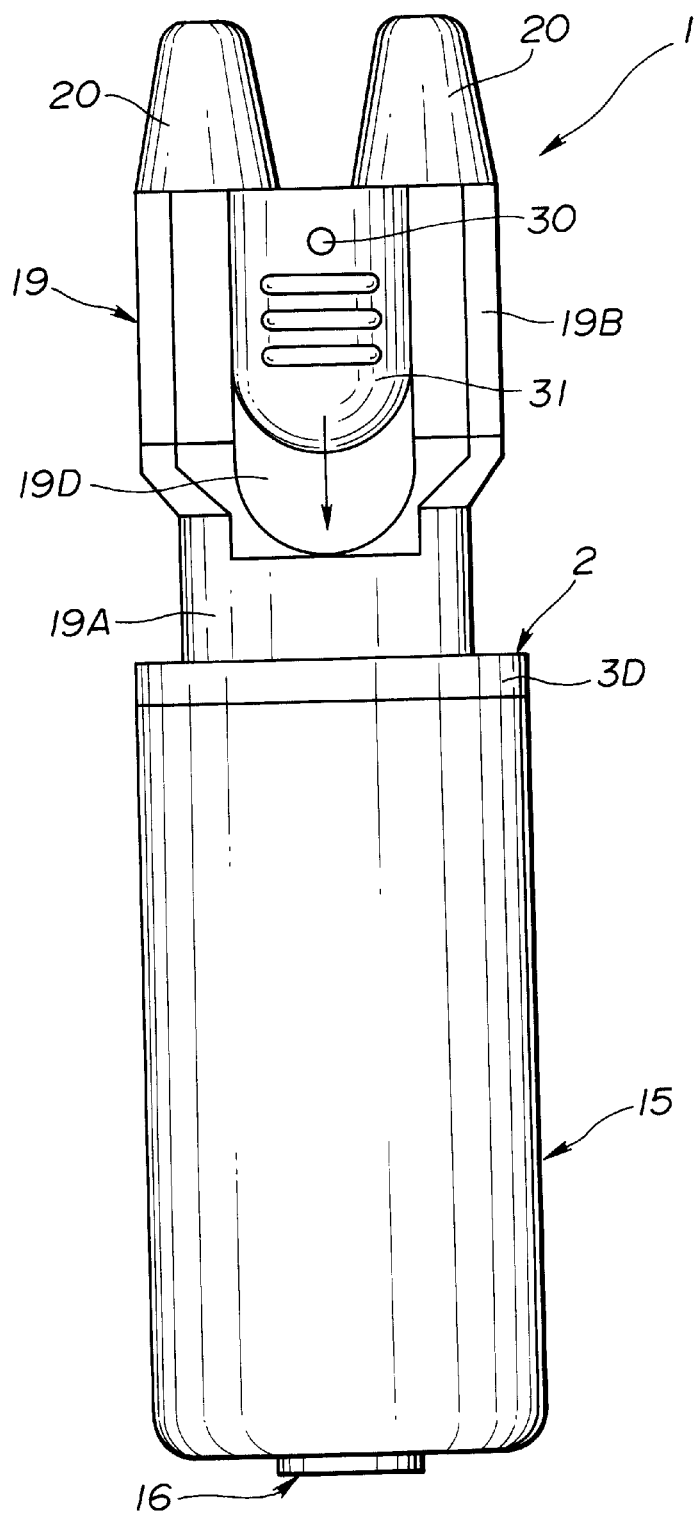
FIG. 1 is a side view showing a medicine administering device for nasal cavities, according to a first embodiment.
Figure 2:
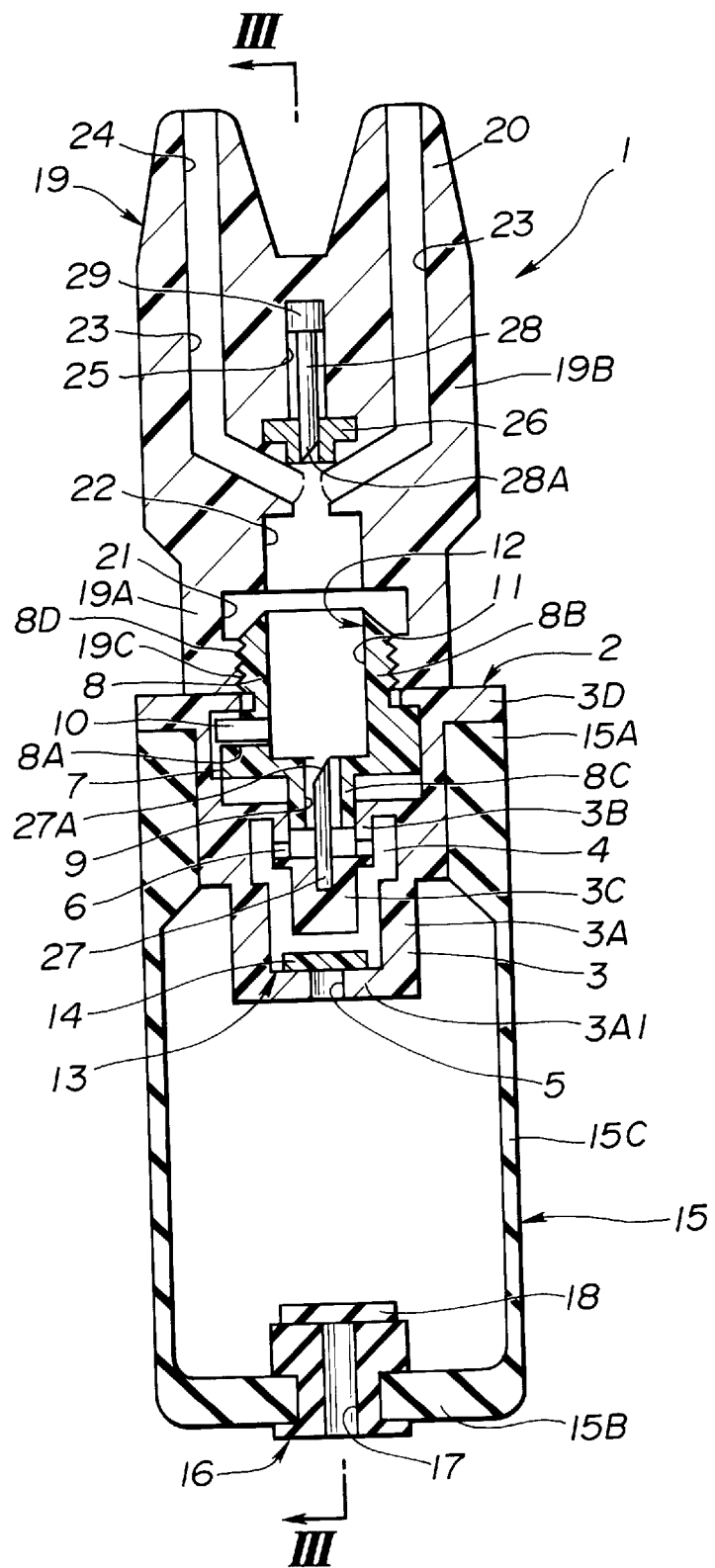
FIG. 2 is a vertical sectional view showing the medicine administering device for nasal cavities, according to the first embodiment.
Figure 3:
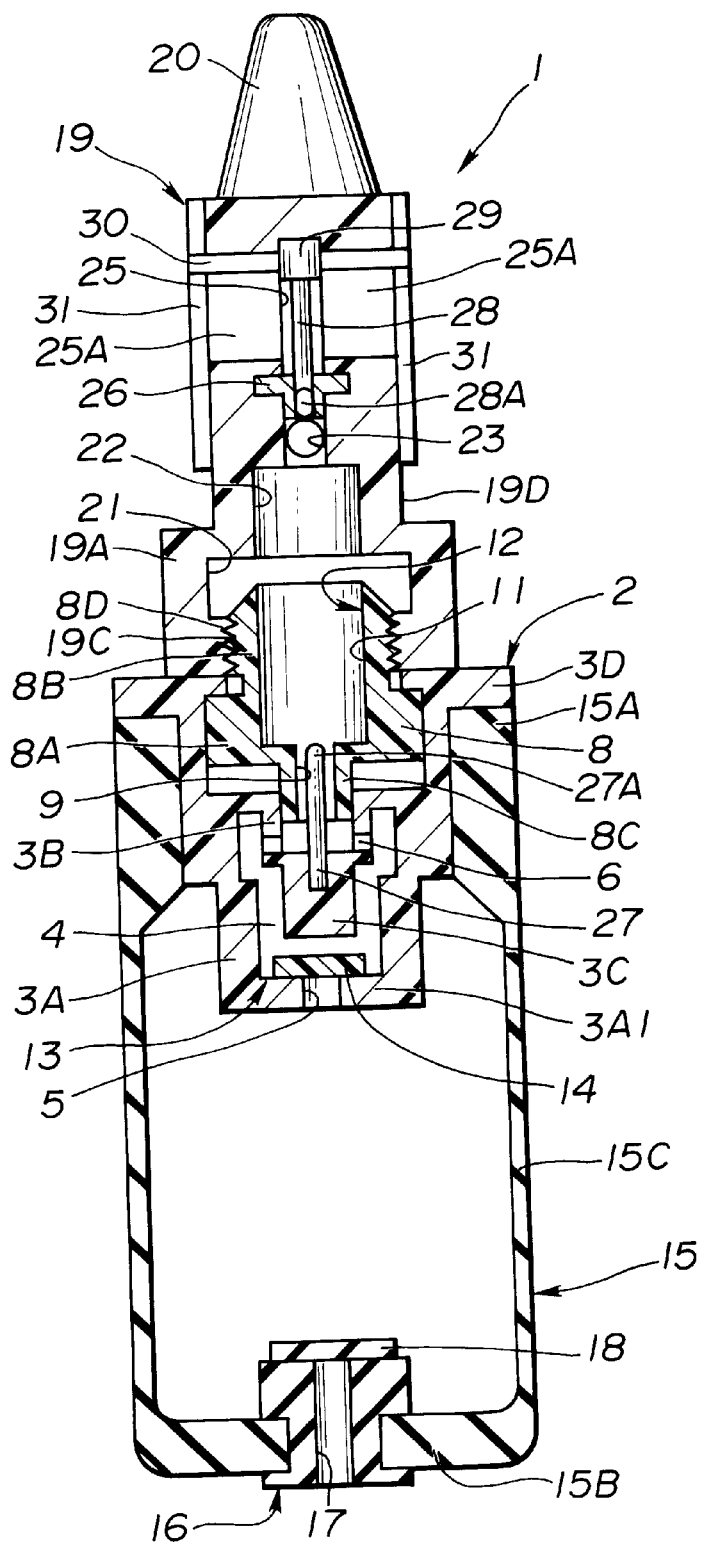
FIG. 3 is a vertical sectional view as viewed from the direction of arrow III—III of FIG. 2.

FIG. 1 shows a medicine administering device for nasal cavities, according to this embodiment. The medicine administering device 1 for nasal cavities generally comprises a capsule holder 2 having a movable member 8 disposed at an axial center of the device 1 so as to hold a capsule K at an upper position in a fixed member 3; a pump section 15 disposed to cover the outside of the fixed member 3 of the capsule holder 2 so as to supply air to the capsule holder 2; a medicine spraying section 19 disposed at an upper section of the capsule holder 2 so as to accomplish medicine spraying to left and right nasal cavities of a patient; a first perforating pin 27 disposed in the fixed member 3 so as to form an air inflow hole H1 in the capsule K; and a second perforating pin 28 accommodated in the medicine spraying section 19 so as to form an air outflow hole H2 in the capsule K.

The capsule holder 2 constituting capsule holding means includes the fixed member 3 which is formed into the shape of a double wall cylinder; and the movable member 8 which is located at the inner peripheral side of the fixed member 3 and disposed axially movable relative to the fixed member 3.

The fixed member 3 includes an outer cylindrical section 3A formed into the shape of a cylinder having a bottom and steps which are located coaxially; an inner cylindrical section 3B having a bottom serving as a medicine trapping section 3C; and a flange section 3D formed to be located at an opening section of the outer cylindrical section 3A. The flange section 3D is provided to prevent the movable member 8, which is axially movable along the inner peripheral surface of the outer cylindrical section 3A, from falling out and to position the pump section 15, which is disposed to cover the outer peripheral side of the fixed member 3. Additionally, the outer cylindrical section 3A and the inner cylindrical section 3B are disposed such that the inner cylindrical section 3B, defining an opening section, is connected to the outer cylindrical section 3A at the axially intermediate position, so that an air inflow chamber 4 is formed between the cylindrical sections 3A, 3B.

Furthermore, an air supply passage 5 in communication with the air inflow chamber 4 is formed at the bottom section 3A1 of the outer cylindrical section 3A of the fixed member 3. The first perforating pin 27 is formed projecting toward the medicine spraying section 19 at the medicine trapping section 3C, serving as a bottom section of the inner cylindrical section 3B. Additionally, the inner cylindrical section 3B is formed at its side surface with communication holes 6, 6 through which the inner peripheral side of the inner cylindrical section 3B is in communication with the air inflow chamber 4, in which, for example, four communication holes are formed extending radially. An axially extending engagement groove 7 is formed at the inner peripheral surface of the outer cylindrical section 3A so that a rotation preventing pin 10 (discussed after) may be engaged.

The movable member 8 is disposed axially movable relative to the fixed member 3 within the outer cylindrical section 3A of the fixed member 3. The movable member 8 is formed of a resin material or plastic and formed into the shape of a cylinder having a bottom. The movable member 8 includes a large diameter bottom section 8A which is axially movably supported within the outer cylindrical section 3A; a cylindrical section 8B; and a small diameter projecting section 8C which extends from the bottom section 8A into the inner cylindrical section 3B. The cylindrical section 8B is formed at its outer peripheral surface with an external thread 8D which extends throughout the whole periphery of the cylindrical section 8B. The small diameter projecting section 8C is formed with a pin insertion hole 9 which extends axially to pierce the bottom section 8A so as to be in communication with the inside of the cylindrical section 8B. The first perforating pin 27 is to be inserted in the pin insertion hole 9. Further, the rotation preventing pin 10 projects diametrically from one side of the cylindrical section 8B. The rotation preventing pin 10 is to be engaged with the engagement groove 7 of the fixed member 3, thereby preventing the movable member 8 from rotation relative to the fixed member 3.

The inner peripheral side of the cylindrical section 8B of the movable member 8 serves as an one-side capsule hole 11. The one-side capsule hole 11 is to be incorporated with an other-side capsule hole 22 (discussed after) of the medicine spraying section 19, thereby constituting a capsule accommodating hole 12.

Thus, in the capsule holder 2, the movable member 8 is arranged to be axially movable along the outer cylindrical section 3A of the fixed member 3. Additionally, when the external thread 8D of the movable member 8 is brought into threaded engagement with the internal thread 19C of the medicine spraying section 19, the movable member 8 is automatically raised to the side of the medicine spraying section 19, because the movable member 8 is prevented from being rotated under the action of the rotation preventing pin 10.

In the drawings, 13 designates a supply valve which includes a large diameter valve member 14 disposed at the side of the air inflow chamber 4 and adapted to open and close the air supply passage 5 formed in the fixed member 3. The valve member 14 is adapted to be opened when air is supplied from the pump section 15 and to be seated to block the air supply passage 5 during inhaling.

The pump section 15 serves as pump means, and is formed of a rubber material and formed into the shape of a cylinder having a bottom. The pump section 15 includes an opening section 15A which is relatively thick; a bottom section 15B; and a pressing section 15C containing the peripheral surface of the pump section 15. The opening section 15A is disposed in contact with the flange section 3D located at the opening section of the fixed member 3 so as to be installed to maintain an air-tight seal and so that the almost whole parts of the capsule holder 2 are located inside the pump section 15. Additionally, a suction valve 16 (discussed after) is installed at the central section of the bottom section 15B.

The suction valve 16 includes a suction passage 17 formed at the bottom section 15B of the pump section 15 and located at the central section of the bottom section 15B; and a valve member 18 which is adapted to open and close the suction passage 17. The valve member 18 is adapted to be closed when air is supplied from the pump section 15 and to be opened to suck air into the pump section 15 from outside during inhaling.

Further, the medicine spraying section 19 disposed in the movable member 8 of the capsule holder 2 serves as medicine spraying means and is formed of a resin material or plastic. The medicine spraying section 19 is formed to have such an outer shape that its part of the side of the capsule holder 2 forms a columnar small diameter section 19A, while its part of the opposite side of the capsule holder forms a long columnar large diameter section 19B. The large diameter section 19B is formed with a pair of nasal cavity insertion sections 20, 20 which project from the large diameter section 19B.

Additionally, a movable member screwing hole 21 is formed at the end face of the small diameter section 19A, in which an internal thread 19C is formed at the opening section-side inner peripheral surface of a part defining the movable member screwing hole 21, the internal thread 19C being in threaded engagement with the external thread 8D. The small diameter section 19A is formed at its inner peripheral surface with the other-side capsule hole 22 which cooperates with the one-side capsule hole 11 to constitute the capsule accommodating hole 12. Further, two medicine passages 23, 23 are formed at the deep end section of the other-side capsule hole 22, and are in communication with the other-side capsule hole 22 to extend to bifurcate generally in a U-shape. The tip end sides of the respective medicine passages 23 are located within the nasal cavity insertion sections 20 so as to form independent spraying holes 24, 24.

Further, the large diameter section 19B of the medicine spraying section 19 is formed at its diametrical end faces with guide grooves 19D, 19D which are located perpendicular to the nasal cavity insertion sections 20, 20.

A pin insertion hole 25 including a pair of long holes 25A, 25A (See FIG. 3) is formed at a diametrically central position between the respective medicine passages 23 which axially extend within the medicine spraying section 19, in which the second perforating pin 28 and the like are housed to extend axially. A rubber seal 26 is disposed at a section in which the pin insertion hole 25 is in communication with each medicine passage 23, in which a perforating pin 28 (discussed after) is to be passed through the rubber seal 26.

In the drawings, 27 designates the first perforating pin as first perforating means. The first perforating pin 27 is located at the medicine trapping section 3C of the inner cylindrical section 3B of the fixed member 3 and projects through the pin insertion hole 9 toward the one-side capsule hole 11. The tip end side of the first perforating pin 27 axially extends to form a perforating end 27A in the shape of an inclined cut needle.

Figure 4:
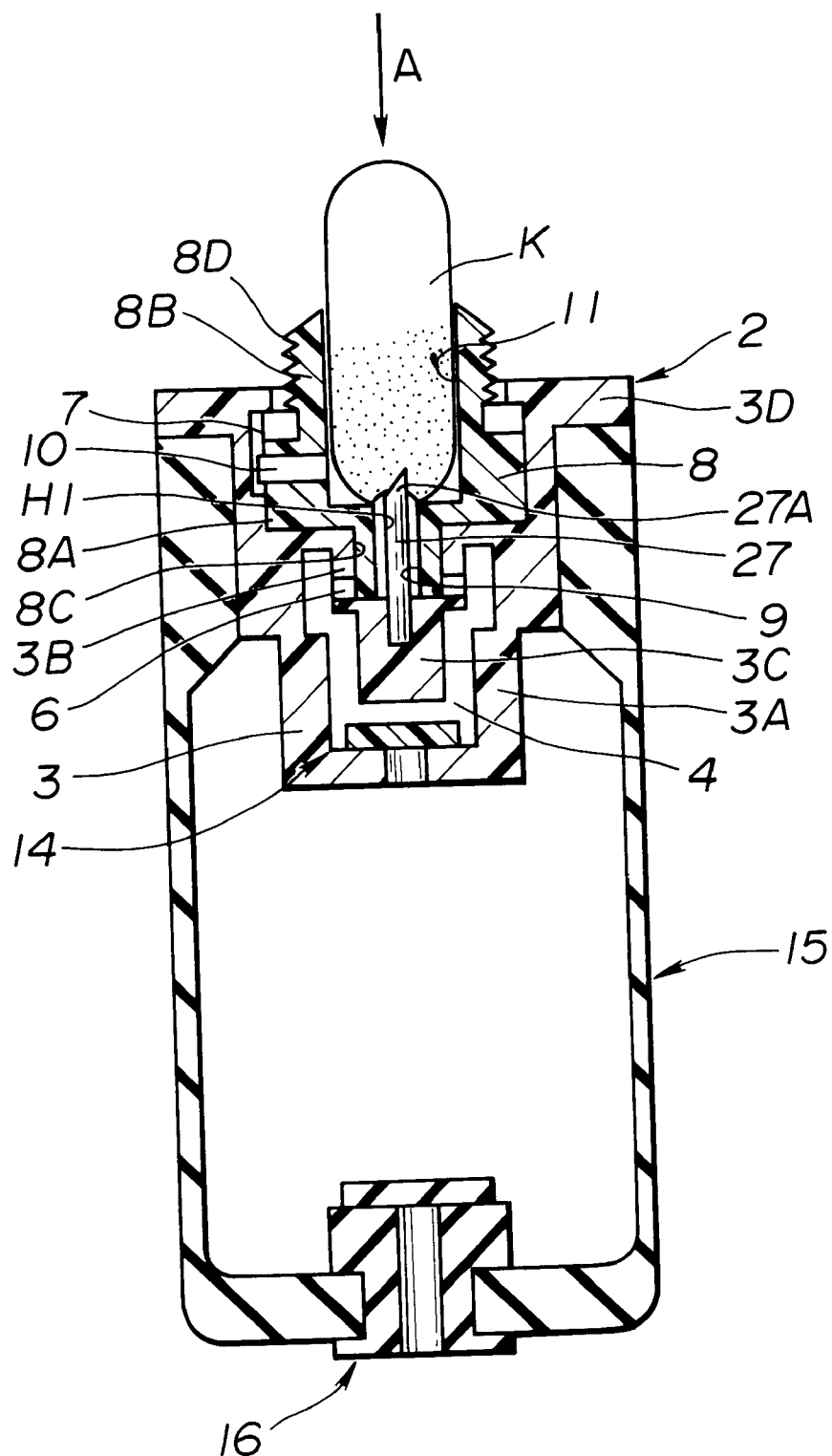
FIG. 4 is a vertical sectional view showing a state in which an air inflow hole has been formed in one side of a capsule with a first perforating pin upon inserting the capsule into a movable member.

Here, when the movable member 8 is located at the side of the pump section 15, the perforating end 27A of the first perforating pin 27 projects into the one-side capsule hole 11, so that the air inflow hole H1 can be formed in the capsule K by pressing the capsule K into the one-side capsule hole 11 in a direction of an arrow A, as shown in FIG. 4. When the movable member 8 is located at the side of the medicine spraying section 19, the perforating end 27A of the first perforating pin 27 is located within the pin insertion hole 9 and does not project into the one-side capsule hole 11, so that the perforating end 27A can be drawn from the air inflow hole H1, as shown in FIG. 6.

In the drawings, 28 designates the second perforating pin, serving as second perforating means, disposed at a position opposite to the first perforating pin 27. The second perforating pin 28 is disposed vertically movable in the pin insertion hole 25, and has a sliding section block 29 disposed at the base end side of the second perforating pin 28 and slidably guided along the pin insertion hole 25. The tip end side of the second perforating pin 28 pierces the rubber seal 26 and forms a perforating end 28A. The sliding block 29 is formed with arm sections 30, 30 which diametrically extend respectively through the long holes 25A, 25A. The tip end sides of the respective arm sections 30, 30 are provided with sliding plates 31, 31 which slide respectively on the guide grooves 19D, 19D of the medicine spraying section 19. By moving the respective sliding plates 31 in the direction of an arrow B in FIG. 1, the sliding block 29 and the perforating pin 28 are moved along the pin insertion hole 25 in the direction of the arrow B, so that the air outflow hole H2 is formed in the capsule K with the perforating end 28A.

The medicine administering device for nasal cavities, according to this embodiment, is arranged as discussed above. Next, operation of the device in use will be discussed with reference to FIGS. 4 to 7.

First, the movable member 8 of the capsule holder 2 is located at the side of the pump section 15, so that the perforating end 27A of the first perforating pin 27 will project into the one-side capsule hole 11. At this time, as shown in FIG. 4, when the capsule K is pressed into the one-side capsule hole 11 from the direction of the arrow A, the air inflow hole H1 is simultaneously formed at an axial one side of the capsule K, since the perforating end 27A of the pin 27 is located at the side of the pump section 15 of the capsule K.

Figure 5:
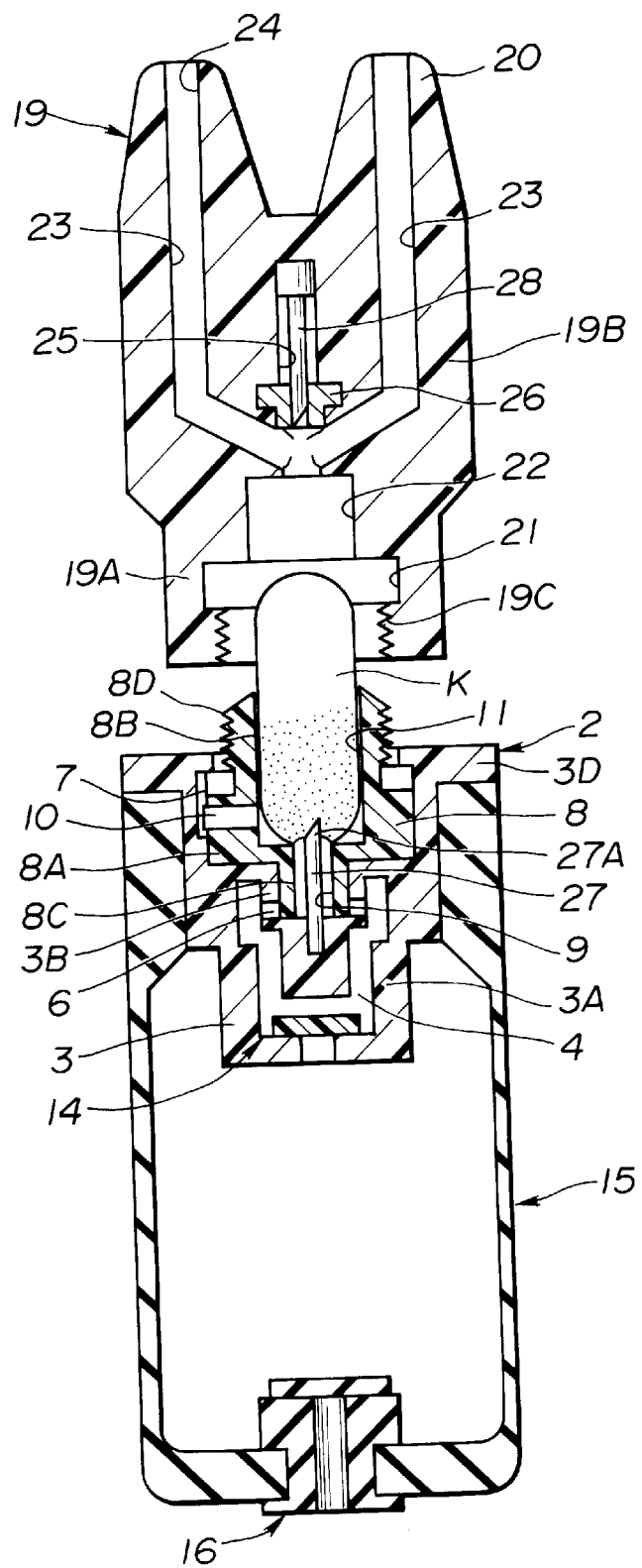
FIG. 5 is a vertical sectional view showing a state before a medicine spraying section is attached to the capsule holder.
Figure 6:
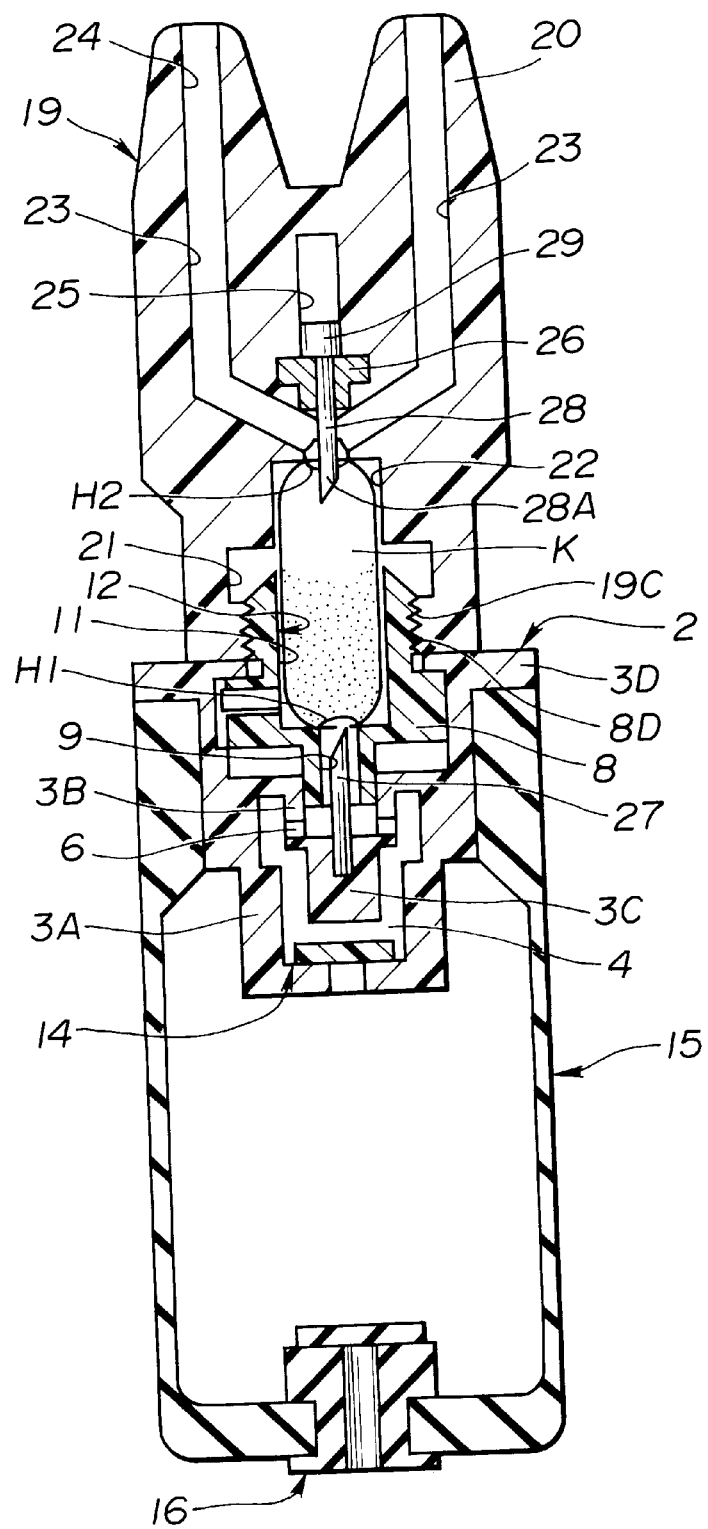
FIG. 6 is a vertical sectional view showing a state in which an air outflow hole has been formed by axially moving a second perforating pin after the medicine spraying section is attached to the capsule holder.
Figure 7:
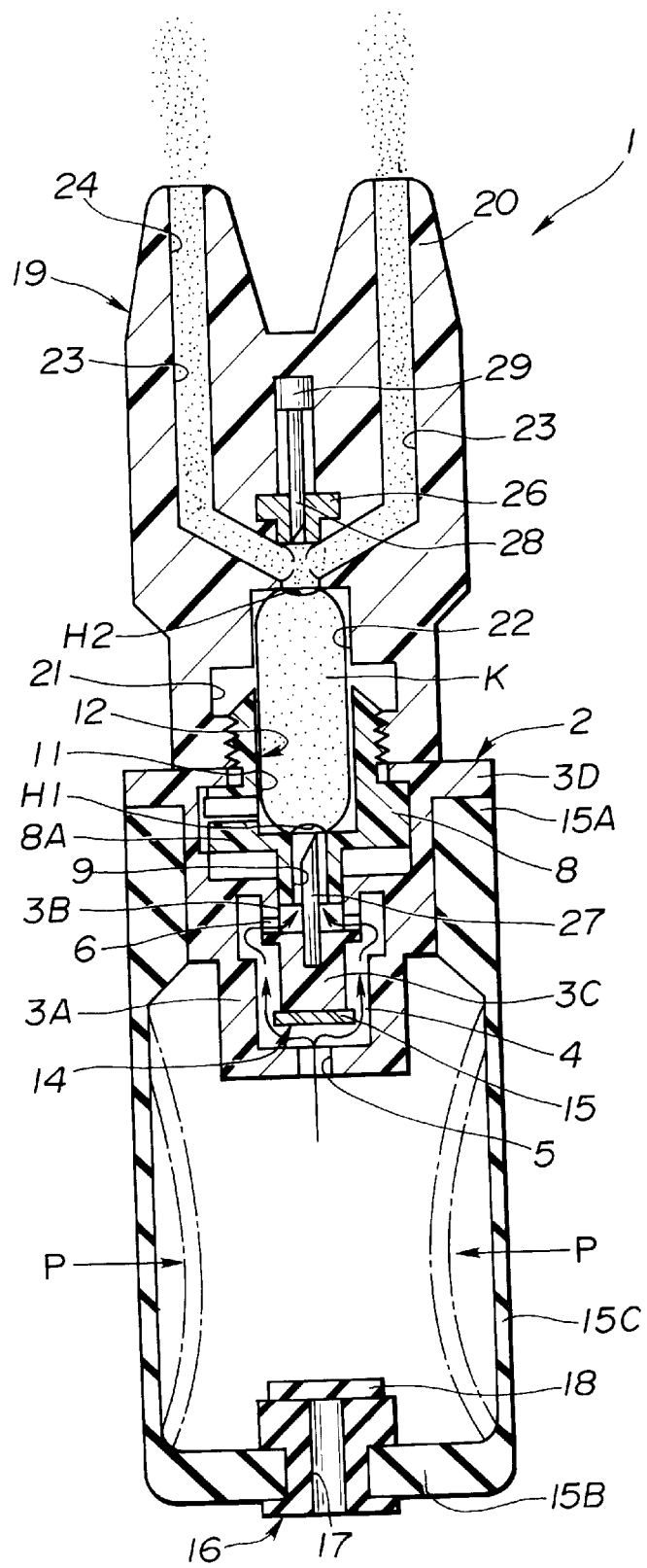
FIG. 7 is a vertical sectional view showing a state in which medicine within the capsule has been sprayed by pressing a pump section.

Subsequently, as shown in FIG. 5, the internal thread 19C of the medicine spraying section 19 is threadedly engaged with the external thread 8D of the capsule holder 2 so that the capsule holder 2 in the state of FIG. 4 attaches to the medicine spraying section 19.

As a result, the movable member 8 of the capsule holder 2 moves to the side of the medicine spraying section 19, while the medicine spraying section 19 is screwed on. When the bottom section 8A of the movable member 8 comes into contact with the flange section 3D, the capsule K is accommodated in the other-side capsule 22 and held in the capsule accommodating hole 12 in a condition in which the capsule K is slightly pressed in an axial direction. At the side of the pump section 15 of the capsule K, the perforating end 27A of the first perforating pin 27 inserted to form the air inflow hole H1 is extracted so that the inside of the capsule K is brought into communication with the air inflow chamber 4 through the air inflow hole H1, the pin insertion hole 9 and the respective communication holes 6.

When the first perforating pin 27 is extracted from the capsule K, the medicine in the capsule K drops to the side of the pump section 15; however, the dropped medicine is trapped (See FIG. 6) because the bottom section of the inner cylindrical section 3B serves as medicine trapping section 3C in this embodiment.

Further, in order to form the air outflow hole H2 located at the other side of the capsule K, the respective sliding plates 31 are moved in a reciprocating manner in the direction of the arrow B in FIG. 1 to move the second perforating pin 28 to the air inflow (pump section 15) side, so that the arm sections 30 and the sliding block 29 move downward along the pin insertion hole 25 while the perforating pin 28 also moves to the side of the pump section 15. At this time, the perforating end 28A of the perforating pin 28 forms the air outflow hole H2 at the axial other side of the capsule K (See FIG. 6).

After completion of the perforating action, the second perforating pin 28 and the like are accommodated within the pin insertion hole 25, so that the perforating end 28A is separate from the respective medicine passages 23, while communication of the pin insertion hole 25 with the respective medicine passage 23 is blocked. Accordingly, the medicine carried together with air during medicine administration is prevented from entering the inside of the pin insertion hole 25.

During medicine administration, the respective nasal cavity insertion sections 20 are inserted into the nasal cavities of the patient. Then, the pressing section 15C of the pump section 15 is squeezed, thereby generating an air stream from the pump section 15. This air stream is applied to the air supply passage 5 so that the valve member 14 of the supply valve 13 is pushed toward the medicine trapping section 3C of the inner cylindrical section 3B, thereby opening the valve. Accordingly, air flows into the capsule K through the air inflow chamber 4, the respective communication holes 6, the pin insertion hole 9 and the air inflow hole H1. Then, air flown into the capsule K stirs the medicine and is sprayed as air mixed with the medicine into the nasal cavities of the patient through the air outflow hole H2, the left and right medicine passages 23 and the medicine spraying holes 24, 24.

Thus, in the medicine administering device for nasal cavities, according to this embodiment, the air inflow hole H1 is formed in the capsule K at a step where the capsule K is installed to the movable member 8 of the capsule holder 2, and then the capsule holder 2 and the medicine spraying section 19 are incorporated with each other through the movable member 8. This moves the movable member 8 to the medicine spraying section 19, thereby rigidly holding the capsule K in the axial direction in the capsule accommodating hole 12 and extracting the perforating end 27A inserted in the air inflow hole H1 of the capsule K. Further, the air outflow hole H2 of the capsule K can be formed with the perforating end 28A by axially moving the second perforating pin 28.

As a result, upon installing the capsule K in the capsule holder 2 and upon making one reciprocating action of the second perforating pin 28 in the axial direction, the air inflow hole H1 and the air outflow hole H2 can be formed, thereby facilitating preparation of the device for medicine administration.

Additionally, all the tools required for perforating the capsule K are housed in the medicine administering device 1 itself, and therefore medicine administration can be performed without detaching any tools at all. This can omit not only attaching and detaching actions for perforating tools but also the possibility of the perforating tools being lost, thereby making it possible to safely handle the medicine administering device.

Additionally, the capsule K is held in the capsule accommodating hole 12 in a state to be slightly pressed in its axial direction, and therefore the capsule K is prevented from movement within the capsule accommodating hole 12. Furthermore, the air inflow hole H1 of the capsule K is brought into tight contact with the pin insertion hole 9, while the air outflow hole H2 is brought into tight contact with the respective medicine passages 23, so that all of the air from the pump section 15 can be flown into the capsule K. Accordingly, medicine can be introduced from the air outflow hole H2 to the respective medicine passages 23, and therefore the amounts of the medicine sprayed from the respective spraying holes 24 become stable so that almost all of the medicine in the capsule K can be administered into the left and right nasal cavities of the patient. As a result, trouble to the patient during medicine administration actions can be largely reduced.

Further, after the air inflow hole H1 of the capsule K is formed, the medicine trapped in the medicine trapping section 3C of the inner cylindrical section 3B serving as the medicine trapping section is conveyed with air from the pump section 15 when air and the medicine are sprayed during the medicine administration action, so that the medicine can be supplied together with the medicine in the capsule K into the left and right nasal cavities of the patient. As a result, the amount of the medicine to be left in the medicine administering device 1 for nasal cavities can be reduced, and therefore the predetermined amount of the medicine within the capsule K can be securely administered to the patient, while reducing the frequency of cleaning of the medicine administering device 1 for nasal cavities.

The medicine administering device 1 for nasal cavities, according to this embodiment, is arranged such that the air inflow hole H1 and the air outflow hole H2 in the capsule in the axial direction are formed respectively by the perforating pins 27, 28, and therefore the length of each pin 27, 28 can be decreased, thereby reducing the longitudinal dimension of the whole medicine administering device 1 for nasal cavities.

Further, in the medicine administering device 1 for nasal cavities, the pump section 15 is installed to cover the outer peripheral side of the fixed member 3 of the capsule holder 2, in which the opening section 15A of the pump section 15 is in contact with the flange section 3D of the fixed member 3. Accordingly, only the medicine spraying section 19 is exposed outside of the pump section 15, thereby largely reducing the axial dimension of the medicine administering device 1 for nasal cavities. Consequently, the medicine administering device 1 for nasal cavities is compact, is easily carried, and is easy to handle.

While the medicine passage 23 formed in the medicine spraying section 19 is bifurcated to form tip ends which serve respectively as the spraying holes 24, 24 so as to make possible it to simultaneously administer the medicine into the left and right nasal cavities of the patient in the above-mentioned embodiment, the present invention is not limited to this, so that one medicine passage may be formed to be alternately inserted into the left and right nasal cavities.

Additionally, while the rotation preventing pin 10 is disposed as a separate member to the movable member 8 of the capsule holder 2, it may be formed integrally with the movable member 8 of the capsule holder 2. Furthermore, while each of the fixed member 3 and the movable member 8 have been shown as an integral molded body, it is a matter of course that each of them may be formed by assembling parts in view of circumstances.

As discussed above, the medicine administering device for nasal cavities, according to the present invention, is applicable where fine granular medicine, filled in a capsule, is inhaled upon breaking the above-mentioned capsule, or where powder-like medicine filled in a capsule is inhaled upon breaking the capsule.

We claim:

1. A medicine administering device for nasal cavities, comprising:
   a capsule holder including a fixed member and a movable member which is slidably fitted in and axially movable relative to said fixed member, said movable member including a first threaded portion;
   a pump section mounted to said fixed member of said capsule holder to supply air toward said capsule holder;
   a medicine spraying section including a second threaded portion for threaded engagement with said first threaded portion of said movable member of said capsule holder, said medicine spraying section having a medicine passage with a spraying hole tip so as to spray medicine within a capsule into a nasal cavity of a patient under the influence of air supplied from said pump section;
   a first perforator mounted in said fixed member for insertion into an end of the capsule; and
   a second perforator mounted in said spraying section for insertion into an opposite end of the capsule;
   wherein said movable member is movable in a direction away from said first perforator during threaded engagement of said spraying section and said movable member, thereby retracting said first perforator from the capsule.

2. A medicine administering device for nasal cavities, as claimed in claim 1, wherein the medicine passage is bifurcated to form two portions, each portion having a tip end that serves as a separate spraying hole.

3. A medicine administering device for nasal cavities, as claimed in claim 1, wherein said capsule holder is located on a side of said device that includes said pump section prior to attachment of said capsule holder and said medicine spraying section to each other, and said capsule holder is located on a side of said medicine spraying section after said medicine spraying section is threadedly engaged to said movable member.

4. A medicine administering device for nasal cavities, as claimed in claim 1, wherein said pump section is disposed to cover an outer peripheral side of said fixed member of said capsule holder.

5. A medicine administering device for nasal cavities, as claimed in claim 1, wherein said capsule holder includes a medicine trapping section for trapping the medicine to drop to a side of device that includes said pump section.

6. A medicine administering device for nasal cavities, as claimed in claim 2, wherein said capsule holder is located on a side of said device that includes said pump section prior to attachment of said capsule holder and said medicine spraying section to each other, and said capsule holder is located on a side of said medicine spraying section after said medicine spraying section is threadedly engaged to said movable member.

7. A medicine administering device for nasal cavities, as claimed in claim 2, wherein said pump section is disposed to cover an outer peripheral side of said fixed member of said capsule holder.

8. A medicine administering device for nasal cavities, as claimed in claim 3, wherein said pump section is disposed to cover an outer peripheral side of said fixed member of said capsule holder.

9. A medicine administering device for nasal cavities, as claimed in claim 2, wherein said capsule holder includes a medicine trapping section for trapping the medicine to drop to a side of device that includes said pump section.

10. A medicine administering device for nasal cavities, as claimed in claim 3, wherein said capsule holder includes a medicine trapping section for trapping the medicine to drop to a side of device that includes said pump section.

11. A medicine administering device for nasal cavities, as claimed in claim 4, wherein said capsule holder includes a medicine trapping section for trapping the medicine to drop to a side of device that includes said pump section.

12. A medicine administering device for nasal cavities, comprising:
   a capsule holder including a fixed member, a movable member which is slidably fitted in and axially movable relative to said fixed member, and a hole for holding a medicine capsule, said movable member including a first threaded portion;

a pump section mounted to said fixed member of said capsule holder to supply air toward said capsule holder;

a medicine spraying section including a second threaded portion for threaded engagement with said first threaded portion on said movable member, said medicine spraying section having a first medicine passage whose tip end serves as a first spraying hole, and a second medicine passage whose tip end serves as a second spraying hole, a generally Y-shaped medicine passage connected with said first and second medicine passages, and a third passage portion connected with said hole of said capsule holder;

a first perforator pin mounted in said fixed member for insertion into an end of a capsule; and a second perforator mounted in said spraying section for insertion into an opposite end of the capsule, said second perforator being insertable through said third passage portion of said medicine spraying section into the capsule;

wherein said movable member is movable in a direction away from said first perforator during threaded engagement of said spraying section and said movable member, thereby retracting said first perforator from the capsule.

* * * * *